United States Patent [19]

Akimura et al.

[11] 4,332,878

[45] Jun. 1, 1982

[54] PHOTOGRAPHIC IMAGE-FORMING METHOD

[75] Inventors: Yoshitaka Akimura; Shigeo Hirano; Hiroyuki Mifune; Eiichi Okutsu, all of Minami-ashigara, Japan

[73] Assignee: Fuji Photo Film Co., Ltd., Minami-ashigara, Japan

[21] Appl. No.: 259,277

[22] Filed: Apr. 30, 1981

[30] Foreign Application Priority Data

Apr. 30, 1980 [JP] Japan ................................. 55-57269

[51] Int. Cl.³ ............................ G03C 5/30; G03C 1/06
[52] U.S. Cl. .................................... 430/264; 430/267; 430/434; 430/443; 430/485; 430/448; 430/599; 430/959; 430/613; 430/405
[58] Field of Search ............... 432/264, 267, 302, 566, 432/405, 448, 249, 599, 434, 440, 441, 443, 484, 485, 957, 959, 960, 613

[56] References Cited

U.S. PATENT DOCUMENTS

| | | | |
|---|---|---|---|
| 3,972,719 | 8/1976 | Vanreusel et al. | 430/440 |
| 4,221,857 | 9/1980 | Okutsu et al. | 430/264 |
| 4,255,510 | 3/1981 | Simons | 430/957 |

*Primary Examiner*—Mary F. Downey
*Attorney, Agent, or Firm*—Sughrue, Mion, Zinn, Macpeak and Seas

[57] ABSTRACT

A photographic image-forming method comprising imagewise exposing a silver halide photographic light-sensitive element containing a specific hydroquinone derivative in the silver halide emulsion layer of substantially the surface latent image type or at least one hydrophilic colloid layer thereof and then developing the exposed light-sensitive element in the presence of a specific hydrazine compound. The method forms a photographic image having markedly high negative gradation.

21 Claims, No Drawings

PHOTOGRAPHIC IMAGE-FORMING METHOD

FIELD OF THE INVENTION

This invention relates to a photographic image-forming method using a silver halide photographic light-sensitive element. More particularly, it relates to a method of developing a silver halide photographic light-sensitive element to provide a markedly high contrast negative image and, furthermore, a dot image having good dot quality and wide screen range.

BACKGROUND OF THE INVENTION

A method of obtaining high contrast and negative photographic characteristics by adding a hydrazine compound to a silver halide photographic emulsion is disclosed in U.S. Pat. No. 2,419,975. This specification describes that when a hydrazine compound is added to a silver chlorobromide emulsion and development is performed with a developer having as high pH as 12.8, markedly high contrast photographic characteristics (gamma ($\gamma$) is more than 10) can be obtained.

Such strong alkali developers having pHs of near 13, however, are unstable because they are easily oxidized by air and thus cannot be stored or used for a long period of time. Furthermore, it is known that dot quality and wide screen range which are sufficient for use in a plate-making process using a contact screen cannot be obtained only by increasing the contrast to such high levels that $\gamma$ is 10 or more. Furthermore, it is known that in order to obtain sufficient dot quality and wide screen range, infectious development characteristics are necessary which are obtained in developing by the use of an unstable lith developer containing a low concentration of sulfite.

British Pat. No. 1,376,600 discloses a method for obtaining photographic characteristics preferred for reproduction of a dot image or line original, by the use of a stable developer. This specification describes that development of a silver halide light-sensitive element with a developer containing (1) a p-dihydroxybenzene derivative, (2) at least 5 g/l of sulfite ions, and (3) a nitroindazole or nitrobenzimidazole compound provides an image having good dot quality. In accordance with this method, however, the dot quality obtained is inferior to that obtained using the conventional lith developer; although the developer is stabilized more than the lith developer. Thus, this method is still unsatisfactory as a method of producing a dot photographic original for plate-making. Furthermore, the method has the disadvantage that as the concentration of sulfite is increased in order to increase the stability of the developer, the dot quality is markedly deteriorated.

A method which can be used to obtain photographic characteristics preferred for reproduction of a dot image by the use of a stable developer is disclosed in U.S. Pat. No. 4,221,857. This method comprises imagewise exposing a light-sensitive element containing a silver halide emulsion of materially the surface latent image type and an acylhydrazine compound, and then developing the thus-exposed light-sensitive element with dihydroxybenzenes in the presence of polyalkylene oxides.

In accordance with this method, a dot image can be obtained which is increased in intensity to higher levels than that obtained by a combination of the conventional lith photographic light-sensitive element and lith development. Furthermore, the image is free from the fringe effect. This method, however, cannot provide such wide screen range as obtained by the conventional lith development.

More specifically, in order to obtain a low fringe dot image by converting the degree of blackening density into the magnitude of dot area by the use of a contact screen, it is necessary that the continuous gradation of the lith light-sensitive element be sufficiently high. Difference between the logarithmic value of exposure amount to provide blackened area of 5% and the logarithmic value of exposure amount to provide blackened area of 95%, i.e., screen range, is theoretically determined by the density pattern of the contact screen used. Wide screen range is preferred, since when the screen range is wide, gradation of original image can be correctly converted to dot image. In other words, when the screen range is narrow, only a part of gradation of original image is convertd to dot image. The screen range obtained by a combination of the lith photographic light-sensitive element and lith development is generally narrower than the screen range which is theoretically expected. This is due to the fact that the combination of the lith photographic light-sensitive element and lith development is easily subject to the development-inhibiting effect caused by $Br^{\ominus}$ ions released from those particles developed during development, a local reduction in pH owing to the development reaction, and so forth. That is, the foregoing development-inhibiting effect is increased as where the development occurs actively. In particular, at highly exposed areas, i.e., areas where the blackening dot area is large, small non-blackening areas between dots are apt to be not developed. As a result the packing of maximum points (dots having the largest blackening area) becomes particularly difficult, and the screen range of the maximum point side is narrowed.

Wide screen range reproductivity is necessary for obtaining a high quality print having good gradation reproductivity. The method as described in U.S. Pat. No. 4,221,857 has the disadvantage that it cannot provide wide screen range comparable to that obtained by the combination of the lith photographic light-sensitive element and lith development. The wide screen range cannot be obtained because the sensitivity to the foregoing local development-inhibiting effect is lower than for the foregoing combination, although it can provide good dot quality.

Furthermore, even with the high contrast negative image as described above, there is a need to further increase graininess.

SUMMARY OF THE INVENTION

An object of this invention is to provide a method of forming a photographic image having markedly high negative gradation, by the use of a stable developer.

Another object of this invention is to provide a method of forming a dot image having good dot quality, by the use of a stable developer.

A further object of this invention is to provide a method of forming a dot image having wide screen range, by the use of a stable developer.

Still another object of this invention is to provide a method of forming a dot image having good gradation reproductivity and furthermore good dot image quality.

Still another object of this invention is to provide a method of forming a photographic image of high negative gradation having excellent graininess.

These objects can be attained by imagewise exposing a silver halide photographic light-sensitive element having a silver halide emulsion layer of materially the surface latent image type and containing a compound represented by formula (I) in at least one layer of the emulsion layer and other hydrophilic colloid layers, and then developing the thus-exposed light-sensitive element in the presence of a compound represented by formula (II).

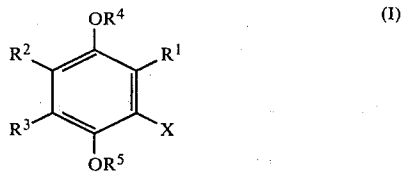

wherein

X represents an indazole radical which is linked to the benzene nucleus through the nitrogen atom at the 1- or 2-position thereof and which may be substituted;

$R^4$ and $R^5$ each represents a hydrogen atom or a group which is hydrolyzed in the presence of an alkali; and $R^1$, $R^2$ and $R^3$ may be the same or different and each represents a hydrogen atom, an alkyl group, an aryl group, an alkylthio group, an arylthio group, a halogen atom, a hydroxy group, an alkoxy group, an aryloxy group, an acyl group, an alkoxycarbonyl group, an amido group, a sulfonamido group, a carbamoyl group, a sulfamoyl group, a heterocyclic radical, or X, and $R^2$ and $R^3$ may combine together to form a ring.

$$R^6NHNHCOR^7 \quad (II)$$

wherein $R^6$ represents an aryl group which may be substituted; and $R^7$ represents a hydrogen atom, an aryl group which may be substituted, and an alkyl group which may be substituted.

DETAILED DESCRIPTION OF THE INVENTION

Silver halide particles used in this invention are substantially of the surface latent image type, in other words, they are not substantially of the internal latent image type. By the term "substantially of the surface latent image type" as used herein is meant that when after imagewise exposure for 1 to 1/100 second, development is performed by Surface Development (A) and Internal Development (B) as described hereinafter, the sensitivity obtained by Surface Development (A) is greater than that obtained by Internal Development (B). The term "sensitivity" as used herein is defined as follows:

$$S = \frac{100}{Eh}$$

wherein S represents sensitivity, and Eh represents an exposure amount required for obtaining a density of $\frac{1}{2}(D_{max}+D_{min})$ (i.e., just halfway between Maximum Density ($D_{max}$) and Minimum Density ($D_{min}$)).

SURFACE DEVELOPMENT (A)

Development is performed at 20° C. for 10 minutes with a developer having the following formulation:

| | |
|---|---|
| p-Hydroxyphenylglycine | 24 g |
| Sodium Carbonate Monohydrate | 60.8 g |
| Sodium Chloride | 2.8 g |
| Water to make | 1 l |

INTERNAL DEVELOPMENT (B)

After processing at about 20° C. for 10 minutes in a bleaching solution containing 3 g/l of red prussiate and 0.0125 g/l of phenosafranine, followed by water-washing for 10 minutes, development is performed at 20° C. for 10 minutes with a developer having the following formulation:

| | |
|---|---|
| N-Methyl-p-aminophenol (hemisulfate) | 5 g |
| Hydroquinone | 10 g |
| Sodium Metaborate Tetrahydrate | 30 g |
| Sodium Sulfite | 75 g |
| Sodium Thiosulfate | 3 g |
| Sodium Hydroxide | 10 g |
| Water to make | 1 l |

When the emulsion of this invention is not substantially of the surface latent image type, it undesirably provides positive gradation as well as negative gradation.

Silver halide which can be used in the silver halide light-sensitive element of this invention includes silver chloride, silver chlorobromide, silver bromide, silver iodobromide and silver chloroiodobromide. Its average grain size is preferably about 0.7 micron or less and more preferably 0.4 micron or less.

The term "average grain size" is generally used in the art of silver halide photographic science and thus can be easily understood by one skilled in the art. By the grain size is meant a grain diameter when the grain is spherical or similar to a ball. When the grain is cubic, the value of (edge length)$\times \sqrt{4/\pi}$ is designated as the grain size. The average grain size is determined based on the algebraic average or geometric average of grain projected areas. A method of determining the average grain size is described in detail in C. E. K. Mees and T. H. James, *The Theory of the Photographic Process*, 3rd Ed., pages 36 to 43, Macmillan (1966).

It is advantageous to use gelatin as a binder or a protective colloid of the photographic emulsion, although other hydrophilic colloids can be used. Substances which can be used include proteins such as gelatin derivatives, graft polymers of gelatin and other polymers, albumin, and casein; cellulose derivatives such as hydroxyethyl cellulose, carboxymethyl cellulose, and cellulose sulfates; sugar derivatives such as sodium alginate and starch derivatives; and hydrophilic synthetic homo- or copolymers, such as polyvinyl alcohol, partial acetal of polyvinyl alcohol, poly-N-vinyl pyrrolidone, polyacrylic acid, polymethacrylic acid, polyacrylamide, polyvinyl imidazole, and polyvinyl pyrazol.

Gelatins which can be used include lime-treated gelatin, acid-treated gelatin, hydrolytic products of gelatin, and enzymic decomposition products of gelatin. These gelatin derivatives can be prepared by reacting gelatin with, for example, acid halide, acid anhydride, isocyanates, bromoacetic acid, alkane sultones, vinylsulfonamides, maleinimides, polyalkylene oxides, and epoxy compounds. Suitable examples of such gelatin derivatives are described in, for example, U.S. Pat. Nos.

2,614,928, 3,132,945, 3,186,846 and 3,312,553, British Pat. Nos. 861,414, 1,033,189 and 1,005,784, and Japanese Patent Publication No. 26845/67.

The foregoing gelatin graft polymers can be prepared by grafting homo- or copolymers of vinyl monomers, such as acrylic acid, methacrylic acid and their derivatives (e.g., esters and amides), acrylonitrile and styrene, on gelatin. Of these gelatin graft polymers, graft polymers of gelatin and polymers having certain compatibility therewith, such as polymers of acrylic acid, methacrylic acid, acrylamide, methacrylamide, hydroxyalkyl methacrylate, etc., are preferred. Examples of such gelatin graft polymers are described in U.S. Pat. Nos. 2,763,625, 2,831,767, and 2,956,884, etc.

Typical examples of hydrophilic synthetic homo- or copolymers are described in, for example, West German Patent Application (OLS) No. 2,312,708, U.S. Pat. Nos. 3,620,751 and 3,879,205, and Japanese Patent Publication No. 7561/68.

The silver halide emulsion which is used in this invention is preferably chemically sensitized, although it may not be chemically sensitized. As a method of chemically sensitizing the silver halide emulsion, sulfur sensitization, reduction sensitization and noble metal sensitization are known. Of such noble metal sensitization methods, a gold sensitization method is typical, in which a gold compound, mainly a gold metal complex salt, is used. In addition to such gold complex salts, complex salts of platinum, palladium, iridium, etc., are advantageously used.

The reduction sensitization method can be used to such an extent not to produce fog which is undesirable for practical use.

These chemical sensitization methods are described in Glafkides, *Chemie et Photographique*, Paul Montel; Zelikman, *Making and Coating Photographic Emulsion*, The Focal Press (1964); and H. Frieser Ed., *Die Grundlagen der Photographischen Prozesse mit Silberhalogeniden*, Akademische Verlagsgesellschaft (1968).

Sulfur sensitizers which can be used include thiosulfates, thioureas, thiazoles and rhodanines. Suitable examples of such sulfur sensitizers are described in U.S. Pat. Nos. 1,574,944, 2,410,689, 2,278,947, 2,728,668 and 3,656,955.

Reduction sensitizers which can be used include stannous salts, amines, formamidinesulfinic acid, and silane compounds. Suitable examples of such reduction sensitizers are described in U.S. Pat. Nos. 2,487,850, 2,518,698, 2,983,609, 2,983,610 and 2,694,637.

For noble metal sensitization, complex salts of Group VIII metals, such as platinum, iridium and palladium, of the Periodic Table can be used. Examples of such complex salts are described in U.S. Pat. No. 2,448,060, British Pat. No. 618,061, etc.

The photographic emulsion of this invention can be prepared by methods as described in P. Glafkides, *Chimie et Physique Photographique*, Paul Montel (1967); C. F. Duffin, *Photographic Emulsion Chemistry*, The Focal Press (1966); V. L. Zelikman et al., *Making and Coating Photographic Emulsion*, The Focal Press (1964), etc. Any of an acidic method, a neutral method, an ammonia method, etc., can be used. As a method of reacting a soluble silver salt and a soluble halide, any of a one-side mixing method, a simultaneous mixing method and a combination thereof can be used.

In addition, a method in which particles are formed in the presence of excessive silver ions, i.e., so-called reverse mixing method can be used. Furthermore, a method in which the pAg in a liquid phase where silver halide is formed is maintained constant, i.e., so-called controlled double jet method, which is one of the simultaneous mixing methods, can be used. In accordance with this controlled double jet method, an emulsion of silver halide having a regular crystal form and a nearly uniform grain size can be obtained.

Silver halide grains in the photographic emulsion used in the present invention may have a comparatively broad size distribution but, preferably, have a narrow grain size distribution. In particular, it is preferred that particles constituting 90% of the total weight or number of silver halide particles have grain sizes falling within the range of average grain size ±40%. In general, such an emulsion is called a single-dispersion emulsion.

Silver halide particles in the photographic emulsion may be in a regular crystal form, such as a cubic form and an octahedral form, an irregular crystal form, such as a spherical form and a plate-like form, or in a composite form of such regular and irregular crystal forms. They may be a mixture of particles having various crystal forms. The inner part and exterior part of the silver halide grains may be different phases or they may comprise a single homogeneous phase.

Formation or physical aging of silver halide particles may be performed in the presence of cadmium salts, zinc salts, lead salts, thallium salts, iridium salts or its complex salts, rhodium salts or its complex salts, iron salts or its complex salts, and the like.

Two or more kinds of silver halide emulsions which are separately prepared may be mixed and used in the practice of this invention.

From the silver halide emulsion are usually removed soluble salts after the precipitate-formation or physical aging. For this purpose, there may be used either a well-known Nudel washing method in which soluble salts are removed by gelling gelatin, or a flocculation method in which inorganic salts comprising polyvalent anions, such as sodium sulfate, anionic surfactants, anionic polymers (e.g., polystyrene sulfonate), and gelatin derivatives (e.g., aliphatic acylated gelatin, aromatic acylated gelatin, and aromatic carbamoylated gelatin) are utilized. Alternatively, the removal of such soluble salts may be omitted.

Addition of a small amount of iodide (e.g., potassium iodide) after the formation of particles, before the chemical aging, after the chemical aging, or before the coating further increases the effects of this invention. The amount of iodide added is preferably from about $10^{-4}$ to $3 \times 10^{-2}$ mol/mol Ag, with the range of from about $10^{-4}$ to $10^{-2}$ mol/mol Ag being particularly preferred.

For the silver halide photographic light-sensitive element for use in the practice of this invention is basically sufficient to have the foregoing silver halide emulsion layer of substantially the surface latent image type. If necessary, the element may include other various auxiliary layers well known in the art, such as an undercoat layer, an overcoat layer, a protective layer, and an intermediate layer.

One of the features of this invention is to use a silver halide photographic light-sensitive element in which one or more of the compounds represented by formula (I) below are introduced into the silver halide emulsion layer or at least one layer of the foregoing auxiliary layers comprising hydrophilic colloid.

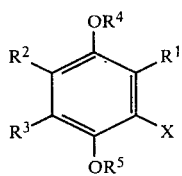

(I)

Compounds represented by formula (I) will be explained in greater detail.

X represents an indazole radical which is linked to the benzene nucleus through the nitrogen atom at the 1- or 2-position thereof, and which may be substituted. Examples of such substituents include a nitro group, an amino group, a carboxy group, a cyano group, a halogen atom (e.g., Br and Cl), a hydroxy group, an alkyl group (preferably containing 1 to 12 carbon atoms, e.g., a methyl group and an ethyl group), an alkoxy group (preferably containing 1 to 12 carbon atoms, e.g., a methoxy group and an ethoxy group), an alkoxycarbonyl group (preferably containing 2 to 13 carbon atoms, e.g., an ethoxycarbonyl group), an alkylthio group (preferably containing 1 to 12 carbon atoms e.g., a methylthio group and an n-butylthio group), an acyl group (preferably containing an alkyl moiety having up to 11 carbon atoms, e.g., an acetyl group), a sulfamoyl group (preferably having an alkyl moiety containing up to 30 carbon atoms, e.g., a dimethylsulfamoyl group), a carbamoyl group (preferably having an alkyl moiety containing up to 30 carbon atoms, e.g., an N,N-dimethylcarbamoyl group), an amido group (preferably having an alkyl moiety containing up to 11 carbon atoms, e.g., an acetamido group), and an acyloxy group (preferably having an alkyl moiety containing up to 11 carbon atoms, e.g., an acetoxy group). Of these substituents, a nitro group, a cyano group and a halogen atom are preferred.

Of the groups represented by X, an indazole group which is substituted by a nitro group at the 5-position thereof is most suitable.

$R^1$, $R^2$ and $R^3$ may be the same or different and each represents a hydrogen atom, a halogen atom (e.g., Cl, Br and I), a hydroxy group, an alkyl group (preferably containing 1 to 18 carbon atoms, e.g., a methyl group, a t-butyl group, a t-octyl group and a pentadecyl group), an aryl group (e.g., a phenyl group and a naphthyl group), an alkylthio group (preferably containing 1 to 18 carbon atoms, e.g., a methylthio group, an octylthio group, a decylthio group, and an octadecylthio group), an arylthio group (e.g., a phenylthio group), an alkoxy group (preferably containing 1 to 18 carbon atoms, e.g., a methoxy group), an aryloxy group (e.g., a phenoxy group), an alkoxycarbonyl group (preferably containing 2 to 19 carbon atoms, e.g., an ethoxycarbonyl group), an acyl group (preferably having an alkyl moiety containing up to 17 carbon atoms, e.g., an acetyl group), an amido group (preferably having an alkyl moiety containing up to 17 carbon atoms, e.g., an acetamido group), a sulfonamido group (preferably having an alkyl moiety or phenyl group containing up to 17 carbon atoms, e.g., a methanesulfonamido group and a benzenesulfonamido group), a carbamoyl group (preferably having an alkyl moiety containing up to 30 carbon atoms, e.g., an N-methylcarbamoyl group, an N,N-dimethylcarbamoyl group, and an N-dodecylcarbamoyl group), a sulfamoyl group (preferably having an alkyl moiety containing up to 30 carbon atoms, e.g., a dimethylsulfamoyl group), a heterocyclic radical (saturated or unsaturated ring containing at least one atom of N, S and O as a hetero atom, preferably a 5- or 6-membered ring, e.g., an imidazolidin-1-yl radical), or X having the same meanings as described above. Of these groups, a hydrogen atom, an alkyl group, an aryl group, an alkylthio group, a halogen atom, an alkoxy group, a carbamoyl group, and X are preferred. A hydrogen atom, an alkyl group, an alkylthio group, and an aryl group are particularly preferred.

$R^2$ and $R^3$ may combine together to form a saturated or unsaturated ring (e.g., a naphthohydroquinone ring, a 5,6-tetramethylenehydroquinone ring, and a 5,6-(1,3-cyclopentylenyl)hydroquinone ring, when named together with the mother nucleus). The saturated or unsaturated ring may be substituted by the foregoing groups described with respect to $R^1$, $R^2$ and $R^3$.

$R^4$ and $R^5$ each represents a hydrogen atom or a group which can be hydrolyzed under alkaline conditions (e.g., an acyl group, such as an acetyl group; a halogen-substituted acyl group, such as a chloroacetyl group and a dichloroacetyl group; an alkoxycarbonyl group, such as an ethoxycarbonyl group; and an aryloxycarbonyl group, such as a phenoxycarbonyl group). Of these groups, a hydrogen atom is preferred.

Examples of the compounds represented by formula (I) are shown below, although this invention is not limited thereto.

Compound I-1
2-(5-Nitro-2-indazolyl)hydroquinone
Compound I-2
6-Methyl-2-(5-nitro-2-indazolyl)hydroquinone
Compound I-3
6-tert-Butyl-2-(5-nitro-2-indazolyl)hydroquinone
Compound I-4
2-(5-Nitro-2-indazolyl)-6-tert-octylhydroquinone
Compound I-5
3,5,6-Trimethyl-2-(5-nitro-2-indazolyl)hydroquinone
Compound I-6
2-(5-Nitro-2-indazolyl)-6-pentadecylhydroquinone
Compound I-7
2-(6-Nitro-2-indazolyl)hydroquinone
Compound I-8
2-(4-Nitro-2-indazolyl)hydroquinone
Compound I-9
2-(7-Nitro-2-indazolyl)hydroquinone
Compound I-10
2-(5-Nitro-2-indazolyl)-5,6-tetramethylenehydroquinone
Compound I-11
5,6-(1,3-Cyclopentylenyl)-2-(5-nitro-2-indazolyl)-hydroquinone
Compound I-12
5-Decylthio-2-(5-nitro-2-indazolyl)hydroquinone
Compound I-13
5-Dodecylthio-2-(5-nitro-2-indazolyl)hydroquinone
Compound I-14
2-(5-Nitro-2-indazolyl)-5-octadecylthiohydroquinone
Compound I-15
2-(5-Nitro-2-indazolyl)-6-phenylhydroquinone
Compound I-16
2-(5-Nitro-2-indazolyl)-5-phenylthiohydroquinone
Compound I-17
5-Chloro-2-(5-nitro-2-indazolyl)hydroquinone
Compound I-18
5-Methoxy-2-(5-nitro-2-indazolyl)hydroquinone
Compound I-19
2-(2-Indazolyl)hydroquinone
Compound I-20
2-(1-Indazolyl)hydroquinone

| |
|---|
| Compound I-21 |
| 2-(5-Chloro-2-indazolyl)hydroquinone |
| Compound I-22 |
| 2-(6-Dimethylsulfamoyl-2-indazolyl)hydroquinone |
| Compound I-23 |
| 2-(5-Cyano-2-indazolyl)hydroquinone |
| Compound I-24 |
| 2-(5-Methyl-2-indazolyl)hydroquinone |
| Compound I-25 |
| 2-(5-Methyl-1-indazolyl)hydroquinone |
| Compound I-26 |
| 2-(5-Nitro-2-indazolyl)naphthohydroquinone |
| Compound I-27 |
| 2,5-Bis(5-nitro-2-indazolyl)hydroquinone |
| Compound I-28 |
| 1,4-Diacetoxy-2-(5-nitro-2-indazolyl)benzene |
| Compound I-29 |
| 1,4-Bischloroacetoxy-2-(5-nitro-2-indazolyl)benzene |
| Compound I-30 |
| 2,3-Bis(5-nitro-1-indazolyl)-1,4-naphthohydroquinone |
| Compound I-31 |
| 2,3,5,6-Tetrakis(5-nitro-1-indazolyl)hydroquinone |
| Compound I-32 |
| 3-(N-Hexylcarbamoyl)-2-(5-nitro-1-indazolyl)-1,4-naphthohydroquinone |
| Compound I-33 |
| 3-(N-Dodecylcarbamoyl)-2-(5-nitro-1-indazolyl)-1,4-naphthohydroquinone |
| Compound I-34 |
| 2-(5-Nitro-1-indazolyl)-3-(N,N-tetramethylenecarbamoyl)-1,4-naphthohydroquinone |

Of these compounds, Compounds I-1, I-2, I-3, I-4, I-7, I-10, I-12, I-15, I-16, I-20, I-27 and I-30 are particularly preferred.

The compounds represented by formula (I) can be prepared, in general, by the following two methods.

One of the methods comprises reacting benzoquinone or a naphthoquinone derivative with an indazole derivative at a temperature of from room temperature to about 100° C. in chloroform or a halogenated hydrocarbon, such as 1,2-dichloroethane, carbon tetrachloride and methylchloroform, in the presence of an acid catalyst, such as p-toluenesulfonic acid, benzenesulfonic acid, methanesulfonic acid, and trifluoromethanesulfonic acid.

In accordance with the other method, chlorine-, bromine- or iodine-substituted benzoquinone or a naphthoquinone derivative is reacted with an indazole derivative at a temperature of from about room temperature to 100° C. in an aprotic solvent, such as acetone, tetrahydrofuran, and dimethylformamide, in the presence of a base, such as potassium carbonate, sodium hydrogencarbonate, and sodium hydride to thereby provide a quinone compound. Then, the quinone compound thus-obtained is reduced by a reductant, such as diethylhydroxyamine and sodium hydrosulfite. (See, for example, *Research Disclosure*, 18227 (1979) and *Liebigs. Ann. Chem.*, 764, 131 (1972), both incorporated herein by reference.)

Benzoquinone derivatives which are used as starting materials can be prepared by the methods described or referred to, for example, in U.S. Pat. Nos. 2,899,334 and 3,700,453, British Pat. Nos. 557,750 and 557,802, U.S. Pat. Nos. 3,043,690, 2,616,893 and 3,009,958, *Helv. Chim. Acta.*, 30, 578 (1947), and *J. Org. Chem.*, 22, 772 (1957), all of which are incorporated herein by reference.

Indazole derivatives can be prepared by the methods described or referred to, for example, in *Org. Syn. Coll. Vol.*, 3, 660 (1955); *Synthesis*, 375 (1972); *Ber.*, 55, 1139 (1922); *J. Chem. Soc.*, 2735 (1960); *Ann.*, 478, 154 (1930); *Ber.*, 43, 2543 (1910); *Ann. Chem.*, 681, 45 (1965); *Ber.*, 53B, 1211 (1920); *J. Prakt. Chem.*, 118, 75 (1928); *Liebigs. Ann. Chem.*, 586, 84 (1954); and *Heterocyclic Compounds*, Bd5, 162-192, John Wiley & Sons, New York (1957), all of which are incorporated herein by reference.

Hereinafter, several preparation examples are shown below:

PREPARATION EXAMPLE 1

Synthesis of Compound I-1

To a mixture of 23.8 g of p-benzoquinone, 32.6 g of 5-nitro-1H-indazole and 250 ml of chloroform was added 40 g of p-toluenesulfonic acid with stirring. After they were reacted at 60° C. for 6 hours, 500 ml of water was added to the reaction solution to precipitate crude crystals. These crude crystals were filtered off.

The thus-obtained crude crystals were dissolved in 200 ml of dimethylformamide and filtered. Thereafter, 800 ml of acetonitrile was added to the filtrate as obtained above to precipitate crystals. On filtering off these crystals, 37.6 g (yield: 69%) of the desired product was obtained. Brown color amorphous product. Melting point is near 250° C. (no definite melting point).

PREPARATION EXAMPLE 2

Synthesis of Compound I-3

To a mixture of 16.4 g of tert-butyl-p-benzoquinone, 16.3 g of 5-nitro-1H-indazole and 200 ml of chloroform was added 20 g of p-toluenesulfonic acid with stirring. After they were reacted at 25° C. for 2 days, 500 ml of water was added to the reaction solution to precipitate crystals. These crystals were filtered off. By fractional recrystallization the crystals from 1,400 ml of methanol, 9.8 g (yield: 30%) of the desired produce was obtained. Orange color needle-like crystal, m.p.: 250° to 254° C.

PREPARATION EXAMPLE 3

Synthesis of Compound I-12

To a mixture of 28 g of 5-decylthio-p-benzoquinone, 16.3 g of 5-nitro-1H-indazole, and 150 ml of chloroform was added 20 g of p-toluenesulfonic acid with stirring. After they were reacted at 60° C. for 5 hours, 500 ml of water was added to the reaction solution to precipitate solids. These solids were filtered off. The resulting chloroform layer was separated, concentrated and separation-purified by silica gel column chromatography (elute, toluene) to obtain 4.3 g (yield: 10%) of the desired product. Brown color flake, m.p.: 118° to 122° C.

PREPARATION EXAMPLE 4

Synthesis of Compound I-27

Compound I-1 (5.4 g) and 11.6 g of manganese dioxide were reacted under reflux for 2 hours in 200 ml of acetone. The manganese dioxide was removed by heat-filtration and washed with hot acetone. After concentration of the resulting filtrate, methanol was added thereto to precipitate 3.5 g of crystals, m.p.: 191° to 194° C.

The thus-obtained benzoquinone compound, 2.1 g of 5-nitro-1H-indazole and 2.9 g of p-toluenesulfonic acid were reacted under reflux for 3 days in 50 ml of chloroform. At the end of the time, 500 ml of water was added to the reaction solution to precipitate crystals. These crystals were filtered off and recrystallized from 120 ml of acetone to obtain 3 g (yield: 53%) of the desired product. Yellow color amorphous product, m.p.: 270° to 272° C. (decomposition).

PREPARATION EXAMPLE 5

Synthesis of Compound I-30

To a mixture of 18.5 g of 2,3-dichloro-1,4-naphthoquinone, 26.6 g of 5-nitro-1H-indazole, and 750 ml of acetone was added 40.5 g of potassium carbonate at room temperature with stirring. After they were reacted at room temperature for 1.5 hours, the resulting reaction solution was filtered. To the filtrate thus-obtained was added 10.9 g of diethylhydroxyamine, and they were further reacted at room temperature for 2 hours. To the reaction solution was added 40 ml of 30% sulfuric acid, and the resulting mixture was decanted. Thereafter, 200 ml of methanol was added, and the resulting mixture was refluxed. The thus-obtained crystals were filtered off, dissolved in 500 ml of acetone, and concentrated. Then, 150 ml of chloroform was added, and the crystals thus-formed were filtered off to obtain 25 g (yield: 64%) of the desired product. Yellow brown color amorphous product, m.p.: 227°–228° C. (decomposition).

The amount of the compound represented by formula (I) being added to the silver halide photographic light-sensitive element is from about $10^{-6}$ to $10^{-1}$ mol/mol Ag, preferably from about $10^{-5}$ to $10^{-2}$ mol/mol Ag, and most preferably from about $1\times10^{-5}$ to $1\times10^{-3}$ mol/mol Ag.

The principal feature of the present photographic image-forming method resides in that a silver halide photographic light-sensitive element containing a compound represented by formula (I) is imagewise exposed and then developed in the presence of a compound represented by formula (II).

Imagewise exposure can be performed by the usual method. As with conventional lith light-sensitive element, it is also possible to apply so-called dot exposure wherein an original image is exposed to light through a contact screen. The method of this invention is advantageous in that in performing the dot exposure, it is not necessary to specifically choose a contact screen suitable for the light-sensitive element for use in the practice of this invention. On the other hand, a specific screen must be used with known lith light-sensitive element as disclosed in Japanese patent application (OPI) No. 22438/76 (the term "OPI" as used herein refers to a "published unexamined Japanese patent application") and U.S. Pat. No. 2,419,975. With the present invention, it is possible to use the same contact screen as used for conventional lith light-sensitive element and obtain screen range having the same width.

The thus-imagewise exposed light-sensitive element is then developed. The terms "development or development processing" and "developer or development processing solution" as used herein include processing with the use of a developer containing a developing agent and said developer. The terms also include so-called alkali activator processing wherein a light-sensitive element previously containing therein a developing agent is processed with an alkaline solution, and said activator processing solution.

Preferred developing agents which can be used in the development processing of this invention include developing agents used in black-and-white photographic processing. In particular, 3-pyrazolidones (e.g., 1-phenyl-3-pyrazolidone), aminophenols (e.g., N-methyl-p-aminophenol), 1-phenyl-3-pyrazolines, dihydroxybenzenes (e.g., hydroquinone) and mixtures thereof are preferred. Of these compounds, it is preferred to use dihydroxy-benzenes (particularly hydroquinone) alone.

The development processing solution of this invention generally contains known preservatives, alkaline agents, pH buffers, antifoggants, etc., in addition to the foregoing developing agents. Additionally, it may contain auxiliary dissolving agents, color-controlling agents, development accelerators, aurfactants, defoaming agents, hard water-softening agents, hardeners, tackifiers, etc. In order to obtain paticularly high dot quality, it is preferred, as described hereinafter, to incorporate polyalkylene oxides and nitroindazoles into the development processing solution of this invention.

The development processing solution of this invention may further contain, as agents to prevent stain resulting from transfer of silver to film, 2-mercaptobenzimidazolesulfonic acids and 2-mercaptobenzothiazolesulfonic acids.

The processing temperature usually ranges between about 18° C. and 50° C. Temperatures higher than 50° C. and lower than 18° C. can be employed.

The optimum pH of the development processing solution varies depending on the type of the compound of formula (II) used. When a developer containing a developing agent is used, the pH is about 9 or more. In particular, the range of about 9.5 to 12.3 is preferred. In the case of the alkali activator, it is sufficient to be about 11.5 or more and preferably about 12.0 or more.

In accordance with the method of this invention, even though a developer containing 0.15 mol/l or more of sulfite ions is used, it is possible to obtain high gradation wherein gamma ($\gamma$) is greater than 10.

The development processing of this invention is performed in the presence of a compound represented by formula (II). For this purpose, various methods can be employed. In one method, a compound represented by formula (II) is introduced into at least one hydrophilic colloid layer of the present silver halide photographic light-sensitive element. In another method, a compound represented by formula (II) is incorporated into a pre-bath prior to development processing. In still another method, a compound represented by formula (II) is incorporated into a development processing solution.

Compounds represented by formula (II):

$$R^6NHNHCOR^7 \qquad (II)$$

are explained in greater detail.

The aryl group represented by $R^6$, which may be substituted, is a monocyclic or bicyclic aryl group. Examples are a benzene ring and a naphthalene ring. Particularly preferred ones are those containing a benzene ring.

The aryl group may be substituted. Preferred examples of such substituents are shown below:

(1) Straight, branched and cyclic alkyl groups, preferably containing 1 to 20 carbon atoms, such as a methyl group, an ethyl group, an isopropyl group, an n-dodecyl group, and a cyclohexyl group;

(2) Aralkyl groups, preferably monocyclic and bicyclic aralkyl groups having an alkyl moiety containing 1 to 3 carbon atoms, such as a benzyl group;

(3) Alkoxy groups, preferably containing 1 to 20 carbon atoms, such as a methoxy group and an ethoxy group;

(4) Amino groups, preferably an —NH$_2$ group and those amino groups mono- or di-substituted by an alkyl group containing 1 to 20 carbon atoms, such as a dimethylamino group and a diethylamino group;

(5) Aryloxy groups, preferably a phenoxy group;

(6) Groups represented by A—X$^0$—$(Y)_{\overline{n}}$;

(7) Groups represented by

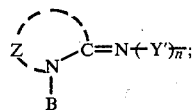

and (8) Groups represented by R$^8$CONHNH—Ar—Y″—.

In the formula: A—X$^0$—$(Y)_{\overline{n}}$ as illustrated above,

Group (6):

(a) X$^0$ is a divalent linking group selected from the following x$_1$ to x$_{11}$:

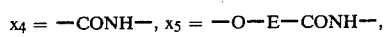

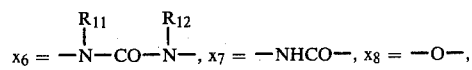

(b) Y is a divalent linking group selected from the following y$_1$ to y$_{11}$; y$_1$=—CONH—, y$_2$=—E—CONH—, y$_3$=—E—, y$_4$=—E—O—E′—, y$_5$=—E—S—E′—, y$_6$=—SO$_2$NH—, y$_7$=—E—SO$_2$NH—, y$_8$=—NHCONH—, y$_9$=—E—NHCONH—, y$_{10}$=—E—O—E′—CONH—, and y$_{11}$=—E—E′—, wherein R$_{11}$ is a hydrogen atom, an aliphatic group (preferably, an alkyl group containing 1 to 20 carbon atoms, a cycloalkyl group containing 3 to 12 carbon atoms, or an alkenyl group containing 2 to 20 carbon atoms), or an aromatic group (preferably, a phenyl group and a naphthyl group), R$_{12}$ is a hydrogen atom or an aliphatic group represented by R$_{11}$, R$_{11}$ and R$_{12}$ may combine with each other to form a ring, with preferred examples of such ring being

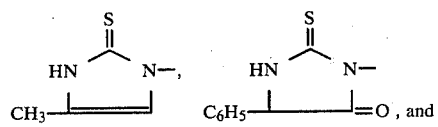

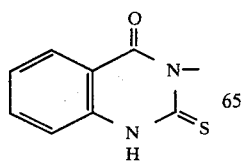

(in this case, A represents hydrogen), when R$_{11}$ and R$_{12}$ do not form a ring, any one of R$_{11}$ and R$_{12}$ is a hydrogen atom, and E and E′ each represents a saturated or unsaturated divalent aliphatic group (e.g., an alkylene group, such as an ethylene group and a 1-methylpropylene group, and an alkenylene group, such as a propenylene group and a butenylene group), a divalent aromatic group (e.g., a phenylene group, a naphthylene group and a 5-amino-1,2-phenylene group), with the exception that in y$_{11}$=—E—E′—, E and E′ are divalent groups different from each other and in x$_{11}$=—E═N—, E is —(CH$_2$)$_m$—CH═ (wherein m is an integer of 0 to 2);

(c) n is an integer of 0 or 1, and when n=1, particularly preferred combinations of X$^0$ and Y are x$_3$-y$_2$, x$_7$-y$_2$, x$_8$-y$_2$, x$_{12}$-y$_3$, x$_3$-y$_7$, x$_5$-y$_9$, x$_9$-y$_9$, and x$_3$-y$_{10}$; and (d) A represents a straight, branched or cyclic alkyl group (preferably containing 1 to 20 carbon atoms, such as a methyl group, a propyl group, and an n-hexyl group), a monocyclic or bicyclic aryl group (e.g., a phenyl group), a monocyclic or bicyclic aralkyl group (preferably containing 7 to 26 carbon atoms, such as a benzyl group), and a heterocyclic radical.

The heterocyclic radical represented by A is a 5- or 6-membered ring containing therein at least one hetero atoms and may be condensed with an aromatic ring, particularly a benzene ring. Particularly, a heterocyclic radical containing at least one nitrogen atom is preferred. Examples are a thiazolyl group, a benzthiazolyl group, an imidazolyl group, a thiazolinyl group, a pyridinyl group, a tetrazolyl group, a benztriazolyl group, an indazolyl group, a benzimidazolyl group, a hydroxytetrazainden-2 or 3-yl; mercapto group-containing heterocyclic groups, such as 2-mercaptobenzthiazolyl group and a 2-mercaptobenzoxazolyl group; and quaternary nitrogen atom-containing heterocyclic radicals, such as 2-methylbenzthiazolinium-3-yl, 2-(N-sulfoethylbenzthiazolinio), and N,N-dimethylbenzimidazolinium-2-yl.

The foregoing groups represented by A may be substituted. Examples of such substituents include:

an alkoxy group (preferably containing 1 to 18 carbon atoms, such as a methoxy group), an alkoxycarbonyl group (preferably containing 2 to 19 carbon atoms, such as an ethoxycarbonyl group), a monocyclic or bicyclic aryl group (e.g., a phenyl group), an alkyl group (preferably containing 1 to 20 carbon atoms, such as a methyl group and a tert-amyl group), a dialkylamino group (preferably containing 1 to 20 carbon atoms, such as a dimethylamino group), an alkylthio group (preferably containing 1 to 20 carbon atoms, such as a methylthio group), a mercapto group, a hydroxy group, a halogen atom, a carboxy group, a nitro group, a cyano group, a sulfonyl group (preferably containing 1 to 20 carbon atoms, such as a methylsulfonyl group), and a carbamoyl group (preferably containing 1 to 20 carbon atoms, such as a carbamoyl group and a dimethylcarbamoyl group).

In the foregoing group represented by Group (7)

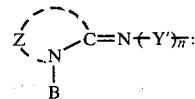

(a) Z is a group of non-metallic atoms and combines with

to form a 5- or 6-membered heterocyclic ring, with suitable examples of such 5- or 6-membered heterocyclic rings being a thiazoline ring, a benzthiazoline ring, a naphthothiazoline ring, a thiazolidine ring, an oxazoline ring, a benzoxazoline ring, an oxazolidine ring, a selenazoline ring, a benzselenazoline ring, an imidazoline ring, a benzimidazoline ring, a tetrazoline ring, a triazoline ring, a thiadiazoline ring, a 1,2-dihydropyridine ring, a 1,2-dihydroquinone ring, a 1,2,3,4-tetrahydroquinoline ring, a perhydro-1,3-oxazine ring, a 2,4-benz[d]oxazine ring, a perhydro-1,3-thiazine ring, a 2,4-benz[d]thiazine ring and a uracyl ring;

(b) B is a hydrogen atom or a saturated or unsaturated aliphatic group [such as an alkyl group (preferably containing 1 to 20 carbon atoms, e.g., a methyl group and an ethyl group), an alkenyl group (preferably containing 2 to 22 carbon atoms, e.g., an allyl group), and an alkynyl group (preferably containing 2 to 20 carbon atoms, e.g., a butynyl group)], which may be substituted by an alkoxy group, an alkylthio group, an acylamino group, an acyloxy group, a mercapto group, a sulfo group, a carboxy group, a hydroxy group, a halogen atom, an amino group, or the like;

(c) Y' has the same meanings as described for Y in Group (6); and (d) n is 0 or 1.

In the group represented by the formula:

$R^8$CONHNH—Ar—Y"—, Group (8):

(a) $R^8$ is the same as $R^7$ as described hereinafter;

(b) —Ar— represents a divalent aryl group, preferably a phenylene group, which may be substituted; and (c) Y" is the same as Y described in Group (6), with divalent linking groups represented by $y_3$ to $y_5$ being particularly preferred.

In formula (II), $R^7$ is a hydrogen atom, an alkyl group which may be substituted, or an aryl group which may be substituted. Substituents which can be used include a halogen atom, a cyano group, a carboxy group, and a sulfo group. Examples of such alkyl and aryl groups are a methyl group, an ethyl group, an n-propyl group, an isopropyl group, a phenyl group, a 4-chlorophenyl group, a 4-bromophenyl group, a 3-chlorophenyl group, a 4-cyanophenyl group, a 4-carboxyphenyl group, a 4-sulfophenyl group, a 3,5-dichlorophenyl group, and a 2,5-dichlorophenyl group.

Of the substituents represented by $R^7$, a hydrogen atom, a methyl group and a phenyl group (including a substituted phenyl group) are preferred, and a hydrogen atom is particularly preferred.

Preferred examples of the compounds represented by formula (II) are described in U.S. Pat. Nos. 4,168,977 and 4,224,401 and British Pat. No. 1,558,946, Japanese Patent Application (OPI) Nos. 52050/80 and 90940/80, Research Disclosure, No. 17626 (Vol. 176, 1978), etc. Of these compounds, those described in U.S. Pat. Nos. 4,168,977 and 4,224,401 are particularly preferred.

Representative examples of the compounds represented by formula (II) are shown below, although this invention is not limited thereto.

Compound II-1

Compound II-2

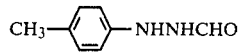

Compound II-3

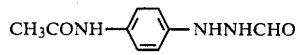

Compound II-4

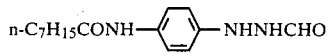

Compound II-5

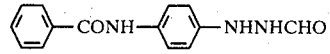

Compound II-6

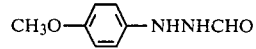

Compound II-7

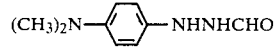

Compound II-8

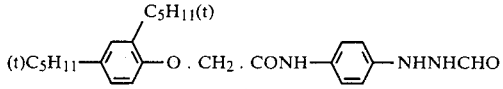

Compound II-9

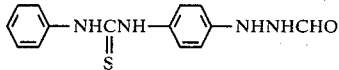

Compound II-10

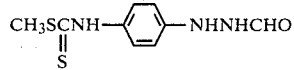

Compound II-11

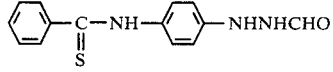

Compound II-12

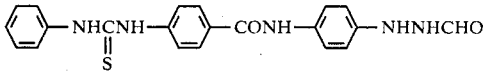

Compound II-13

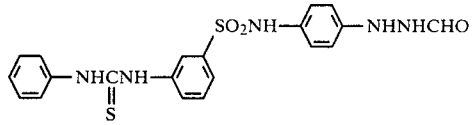

Compound II-14

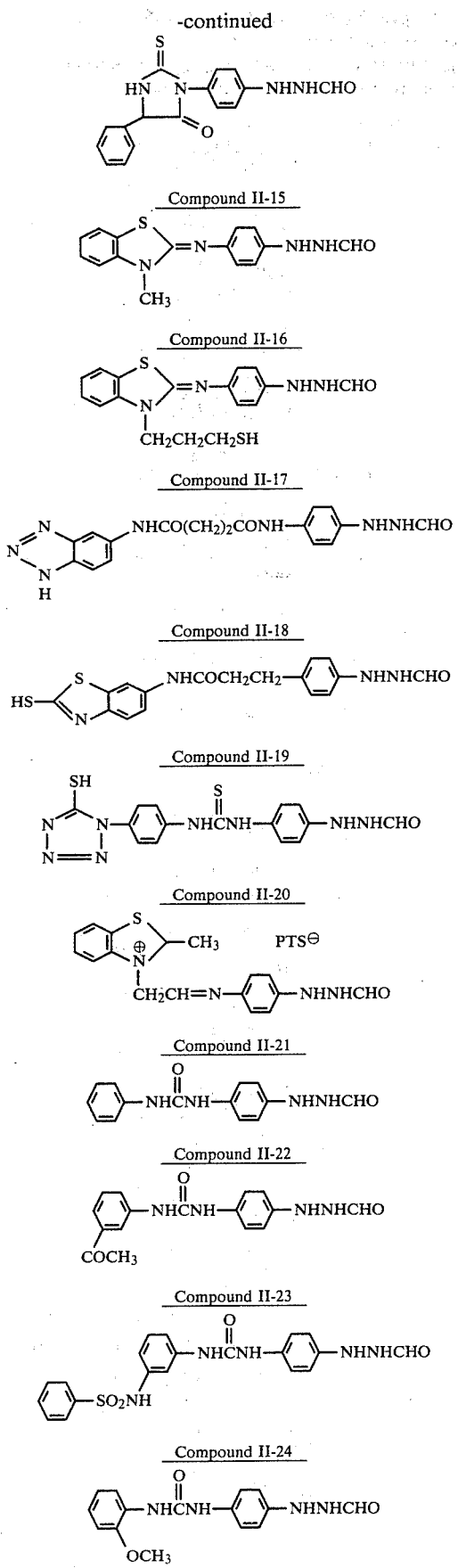
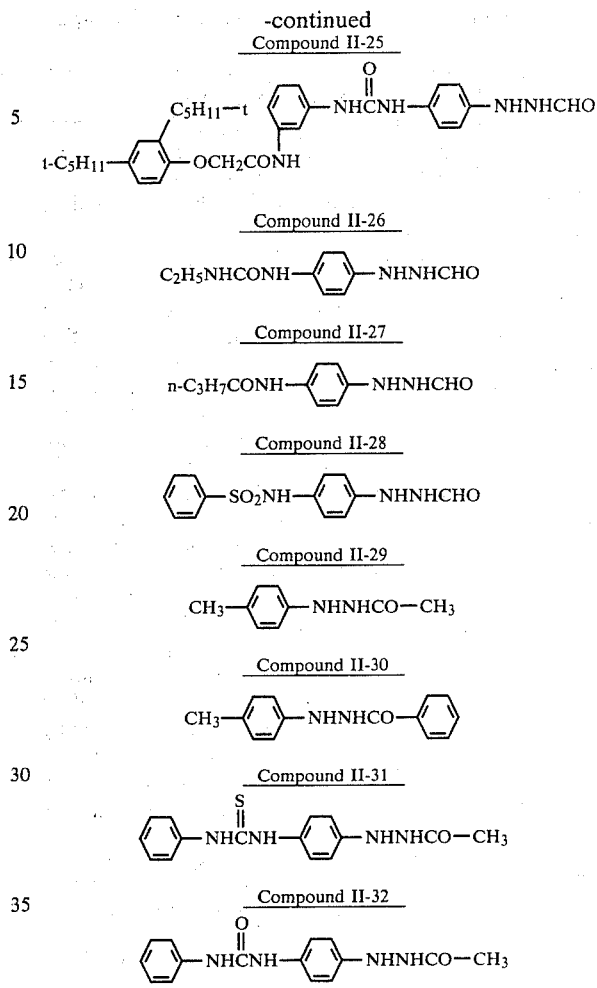

These compounds can be synthesized by methods as described in U.S. Pat. Nos. 4,168,977 and 4,224,401, and British Pat. No. 1,558,946, all of which are incorporated herein by reference.

The amount of the compound represented by formula (II) incorporated into the silver halide light-sensitive element is from about $10^{-8}$ to $10^{-1}$ mol/mol Ag and preferably from about $10^{-6}$ to $5\times 10^{-2}$ mol/mol Ag. When the compound represented by formula (II) is incorporated into silver halide light-sensitive element in an amount of more than the above-defined amount (i.e., more than $10^{-1}$ mol/mol Ag), undesired fog will increase.

In order to incorporate the compound represented by formula (II) into the light-sensitive element, a method which is usually used to add an additive to a photographic emulsion can be employed. For example, when the compound is water-soluble, it is dissolved in water to prepare a suitable concentration of an aqueous solution. When the compound is insoluble or sparingly soluble in water, it is dissolved in a suitable organic solvent exerting no adverse influences on photographic characteristics, which is selected from organic solvents compatible with water, such as alcohols, glycols, ketones, esters, and amides, to prepare a solution. The thus-obtained aqueous solution or organic solution is added to a photographic emulsion or a light-insensitive hydrophilic colloid solution. Additionally, a method which is often used in adding a water-insoluble (so-called oilsoluble) coupler to an emulsion in the form of a dispersion can be employed.

The amount of the compound represented by formula (II) used when introduced into a prebath or development processing solution is from about 5 mg to 5 g, preferably from about 10 mg to 1 g, per liter of the prebath or development processing solution.

Adding hydrazine compounds to the silver halide photographic emulsion or developer is known, as described in U.S. Pat. No. 3,730,727 (wherein a developer comprising ascorbic acid and hydrazine is used), U.S. Pat. No. 3,227,552 (wherein hydrazine is used as an auxiliary developing agent to obtain a direct positive color image), U.S. Pat. No. 3,386,831 (wherein β-monophenylhydrazide of an aliphatic carboxylic acid is used as a stabilizer of a silver halide light-sensitive element), U.S. Pat. No. 2,419,975, Mees, *The Theory of Photographic Process*, 3rd Ed., page 281 (1966), etc.

Although the mechanism of the compound of formula (II) is not sufficiently clear, it is believed that the compound does not act as a halogen acceptor as described in T. H. James, *The Theory of The Photographic Process*, 4th Ed., page 158, Macmillan, because when it is present only at the time of exposure, it does not exhibit its effects. Furthermore, since the light-sensitive element of this invention does not produce an image unless the developing agents as described hereinbefore are applied, the compound does not act as a developing agent. The presence of the compound at the time of development increases the sensitivity and gradation of the light-sensitive element and at the same time, good dots and wide screen range.

In forming a dot image in accordance with the method of this invention, much better dot quality can be obtained by processing in the presence of a polyalkylene oxide compound or its derivative.

Polyalkylene oxides and their derivatives which can be used in this invention have a molecular weight of at least 600. These polyalkylene oxides and their derivatives may be incorporated into either the silver halide light-sensitive element or the developer.

The polyalkylene oxide compounds as used herein include condensates of polyalkylene oxide comprising 10 or more of alkylene oxide containing 2 to 4 carbon atoms, such as ethylene oxide, propylene-1,2-oxide, and butylene-1,2-oxide, preferably ethylene oxide, and compounds containing therein at least one active hydrogen atom, such as water, aliphatic alcohol, aromatic alcohol, aliphatic acid, organic amine and hexitol; and block copolymers of two or more polyalkylene oxides.

Examples of such polyalkylene oxide compounds are as follows:

Polyalkylene glycols, polyalkylene glycol alkyl ethers, polyalkylene glycol aryl ethers, polyalkylene glycol alkylaryl ethers, polyalkylene glycol esters, polyalkylene glycol aliphatic acid amides, polyalkylene glycol amines, polyalkylene glycol block copolymers, and polyalkylene glycol graft polymers.

Not only one polyalkylene oxide chain, but also two or more polyalkylene oxide chains may be contained in the molecular. In this case, the total of alkylene oxide units contained in the molecule should be at least 10, although each polyalkylene oxide chain may comprise less than 10 alkylene oxide units. Where the molecule contains therein two or more polyalkylene oxide chains, these polyalkylene oxide chains may comprise different alkylene oxide units, such as ethylene oxide and propylene oxide. Polyalkylene oxide compounds as used herein preferably contain therein from 14 to 100 of alkylene oxide units.

Examples of polyalkylene oxide compounds which can be used in this invention are shown below:

Compound III-1
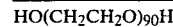
$HO(CH_2CH_2O)_{90}H$

Compound III-2
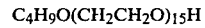
$C_4H_9O(CH_2CH_2O)_{15}H$

Compound III-3
$C_{12}H_{25}O(CH_2CH_2O)_{15}H$

Compound III-4
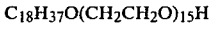
$C_{18}H_{37}O(CH_2CH_2O)_{15}H$

Compound III-5
$C_{18}H_{37}O(CH_2CH_2O)_{40}H$

Compound III-6
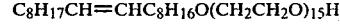
$C_8H_{17}CH=CHC_8H_{16}O(CH_2CH_2O)_{15}H$

Compound III-7
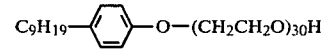

Compound III-8
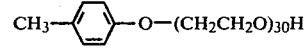

Compound III-9
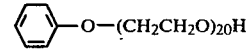

Compound III-10
$C_{11}H_{23}COO(CH_2CH_2O)_{80}H$

Compound III-11
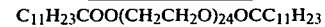
$C_{11}H_{23}COO(CH_2CH_2O)_{24}OCC_{11}H_{23}$

Compound III-12
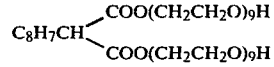

Compound III-13
$C_{11}H_{23}CONH(CH_2CH_2O)_{15}H$

Compound III-14
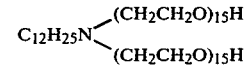

Compound III-15
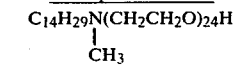

Compound III-16
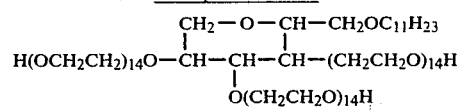

Compound III-17
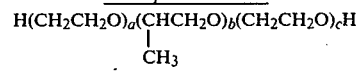

$a + b + c = 50$
$b : a + c = 10 : 9$

Compound III-18

-continued

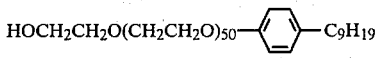

Compound III-19

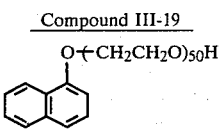

Compound III-20

$HO(CH_2CH_2O)_a(CH_2CH_2CH_2CH_2O)_b(CH_2CH_2O)_cH$
$a + c = 30, b = 14$

Compound III-21

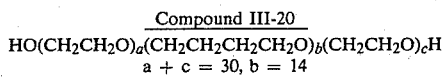

$b = 8, a + c = 50$

Compound III-22

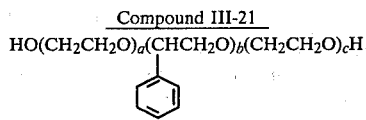

Compound III-23

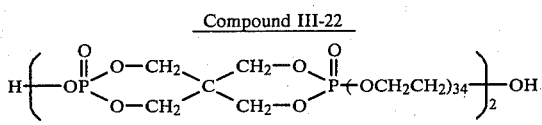

Compound III-24

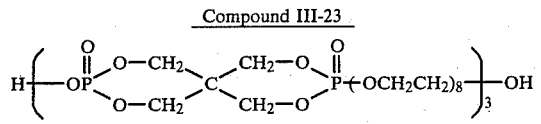

These polyalkylene oxide compounds are described in U.S. Pat. Nos. 4,011,082 and 4,144,069 and Japanese Patent Application (OPI) No. 3217/78, and they can be used alone or in combination with each other.

These polyalkylene oxide compounds can be dissolved in water or a low boiling point organic solvent compatible with water and added to an emulsion at a suitable stage before coating, preferably after chemical aging. Alternatively, they may be added not to the emulsion, but to light-insensitive hydrophilic colloid layers, such as an intermediate layer, a protective layer and a filter layer.

When the foregoing polyalkylene oxide compound is added to a developer, it can be added as a solid, a suitable concentration of an aqueous solution, or as a solution in a low boiling point organic solvent compatible with water.

The polyalkylene oxide compound of this invention can be added to the light-sensitive element in an amount of from about $5 \times 10^{-4}$ to 5 g, preferably from about $1 \times 10^{-3}$ to 1 g, per mol of silver halide.

The polyalkylene oxide compound of this invention can be added to the developer in an amount of about $1 \times 10^{-2}$ g or more, preferably from about $5 \times 10^{-2}$ to 40 g, per liter of the developer.

After the development processing of this invention, known processings are applied.

Fixers having formulations which are generally used can be used in this invention. Fixing agents which can be used include thiosulfuric acid salts, thiocyanic acid salts, and furthermore organic sulfur compounds which are known to be effective as fixing agents. The fixer may contain a water-soluble aluminum salt, etc., as hardeners.

A negative image produced by the method of this invention has good graininess and markedly high gradation wherein gamma ($\gamma$) exceeds 10. Also, a dot image produced by the method of this invention has high dot quality and, at the same time, has screen range equal to or more wide than that obtained by the usual lith light-sensitive element. Thus, the dot image thus-obtained is very useful as a light-sensitive element for printing. Furthermore, this invention is very advantageous in that it can produce high quality photographic images by the use of a stable processing solution. The use of a stable processing solution reduces the amount of handling of solutions which has heretofore been required.

The silver halide photographic light-sensitive element and processing solution as used herein may contain various photographic additives which are known in the art. This invention also includes embodiments wherein such known photographic additives are used.

Hereinafter, some of such known photograhic additives will be explained.

For the purposes of preventing fog in the course of production, storage or photographic processings of the present light-sensitive element and of stabilizing its photographic performance, various compounds can be incorporated thereinto. Antifoggants or stabilizers which can be used include azoles, such as benzothiazolium salts, nitroindazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, and mercaptotetrazoles (particularly, 1-phenyl-5-mercaptotetrazole); mercaptopyrimidines; mercaptotriazines; thioketo compounds, such as oxazolinethion; azaindenes, such as triazaindenes, tetrazaindenes (particularly, 4-hydroxy-substituted (1,3,3a,7)-tetrazaindenes), and pentazaindenes; benzenesulfonic acid, benzenesulfinic acid, and benzenesulfonic acid amide. Of these compounds, benzotriazoles, such as 5-methylbenzotriazole, and nitroindazoles, such as 5-nitroindazole, are particularly preferred. These compounds may be incorporated into processing solutions.

For the puprose of improving dimension stability, a water-insoluble or water-sparingly-soluble synthetic polymer dispersion can be incorporated into the photographic emulsion of this invention. Synthetic polymers which can be used include homo- and copolymers of alkyl acrylate, alkyl methacrylate, alkoxyalkyl acrylate, alkoxyalkyl methacrylate, glycidyl acrylate, glycidyl methacrylate, acrylamide, methacrylamide, vinyl ester (e.g., vinyl acetate), acrylonitrile, olefin and styrene, and copolymers of such monomers and acrylic acid, methacrylic acid, $\alpha,\beta$-unsaturated dicarboxylic acid, hydroxyalkyl acrylate, hydroxyalkyl methacrylate, sulfoalkyl acrylate, sulfoalkyl methacrylate, and styrenesulfonic acid. For example, synthetic polymers as described in, for example, U.S. Pat. Nos. 2,376,005, 2,739,137, 2,853,457, 3,062,674, 3,411,911, 3,488,708, 3,525,620, 3,607,290, 3,635,715, and 3,645,740, and British Pat. Nos. 1,186,699 and 1,307,373, can be used. The high contrast emulsion of this invention is suitable for reproduction of a line image, in which dimension stability is significant. Thus, it is preferred for the present emulsion to contain therein the foregoing polymer dispersion.

The photographic emulsion for use in this invention may be spectral-sensitized with methine dyes and the like. Dyes which can be used include cyanine dye, merocyanine dye, complex cyanine dye, complex merocyanine dye, holopolar cyanine dye, hemicyanine dye, styryl dye, and hemioxonol dye. Particularly preferred examples are cyanine dye, merocyanine dye and complex merocyanine dye. To these dyes can be applied any of nuclei which are usually used for cyanine dyes as basic heterocyclic nuclei. Nuclei which can be applied include a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, and a pyridine nucleus; nuclei comprising the foregoing nuclei and alicyclic hydrocarbon rings fused thereto; and nuclei comprising the foregoing nuclei and aromatic hydrocarbon rings fused thereto, for example, an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus, and a quinoline nucleus. These nuclei may be substituted at the carbon atom or atoms thereof.

To merocyanine and complex merocyanine dyes can be applied, as nuclei having the ketomethylene structure, 5- or 6-membered hererocyclic nuclei, such as a pyrazolin-5-on nucleus, a thiohydantoin nucleus, a 2-thioxazolidin-2,4-dion nucleus, a thiazolidin-2,4-dion nucleus, a rhodanine nucleus, and a thiobarbituric acid nucleus.

Useful sensitization dyes are described in, for example, German Patent 929,080, U.S. Pat. Nos. 2,231,658, 2,493,748, 2,503,776, 2,519,001, 2,912,329, 3,656,959, 3,672,897, and 3,694,217, British Pat. No. 1,242,588, and Japanese Patent Publication No. 14030/69.

These sensitization dyes can be used alone or in combination with each other. In particular, for the purpose of supersensitization, they are often used in combination with each other. Typical examples of such sensitization dyes are described in U.S. Pat. Nos. 2,688,545, 2,977,229, 3,397,060, 3,522,052, 3,527,641, 3,617,293, 3,628,964, 3,666,480, 3,679,428, 3,703,377, 3,769,301, 3,814,609, and 3,837,862, British Pat. No. 1,344,281, and Japanese Patent Publication No. 4936/68, etc.

Together with these sensitization dyes, dyes which per se have no spectral sensitization action, but exhibit high color sensitization, or substances which absorb substantially no visible light, but exhibit supersensitization may be incorporated into the emulsion. For example, aminostilbene compounds substituted by nitrogen-containing heterocyclic rings (described in, for example, U.S. Pat. Nos. 2,933,390 and 3,635,721), aromatic organic acids-formaldehyde condensates (described in, for example, U.S. Pat. No. 3,743,510), cadmium salts, and azaindene compounds can be incorporated. Combinations disclosed in U.S. Pat. Nos. 3,615,613, 3,615,641, 3,617,295 and 3,635,721 are particularly useful.

The photograhic emulsion for use in this invention may contain water-soluble dyes as filter dyes or for various purposes of prevention of irradiation, etc. Water-soluble dyes which can be used include oxonol dye, hemioxonol dye, styryl dye, merocyanine dye, cyanine dye, and azo dye. Of these compounds, oxonol dye, hemioxonol dye and merocyanine dye are useful. Examples of such dyes which can be used are described in British Pat. Nos. 584,609, 1,177,429, Japanese Patent Application (OPI) Nos. 85130/73, 99620/74, 114420/74, and U.S. Pat. Nos. 2,274,782, 2,533,472, 2,956,879, 3,148,187, 3,177,078, 3,247,127, 3,540,887, 3,575,704, 3,653,905 and 3,718,472.

An inorganic or organic hardener may be incorporated into the photographic emulsion of this invention. Hardeners which can be used include chromium salts (e.g., chromium alum and chromium acetate), aldehydes (e.g., formaldehyde, glyoxal, and glutaraldehyde), N-methylol compounds (e.g., dimethylol urea and methyloldimethyl hydantoin), dioxane derivatives (e.g., 2,3-dihydroxydioxane), active vinyl compounds (e.g., 1,3,5-triacryloylhexahydro-s-triazine, bis(vinylsulfonyl)methyl ether, and N,N'-methylenebis[$\beta$-(vinylsulfonyl)propionamide]), active halogen compounds (e.g., 2,4-dichloro-6-hydroxy-s-triazine), mucohalogenic acids (e.g., muchchloric acid and mucophenoxychloric acid), isoxazoles, dialdehyde starch, and 2-chloro-6-hydroxytriazinilated gelatin. These hardeners can be used alone or in combination with each other. Examples are described in U.S. Pat. Nos. 1,870,354, 2,080,019, 2,726,162, 2,870,013, 2,983,611, 2,992,109, 3,047,394, 3,057,723, 3,103,437, 3,321,313, 3,325,287, 3,362,827, 3,539,644 and 3,543,292, British Pat. Nos. 676,628, 825,544, and 1,270,578, German Pat. Nos. 872,153 and 1,090,427, Japanese Patent Publication Nos. 7133/59 and 1872/71, etc.

The photographic emulsion of this invention may contain various known surfactants as auxiliary coating agents or for the purposes of preventing electrification, improving sliding properties, accelerating emulsification-dispersion, preventing adhesion and of improving photographic characteristics.

Surfactants which can be used include nonionic surfactants, such as saponin (steroid-based), polyalkyleneglycol alkyl-amines or -amines, polyethylene oxide adducts of silicon, glycidol derivatives (e.g., alkenylsuccinic acid polyglyceride, and alkylphenol polyglycide), aliphatic acid esters of polyhydric alcohol, and alkylesters, urethanes or ethers of sugar; anionic surfactants containing acidic groups (e.g., a carboxy group, a sulfo group, a phospho group, a sulfate group, and a phosphate group), such as triterpenoid-based saponin, alkyl carboxylates, alkyl sulfonates, alkylbenzenesulfonates, alkylnaphthalenesulfonates, alkylsulfates, alkyl phosphates, N-acyl-N-alkyltaurines, sulfosuccinates, sulfoalkyl polyoxyethylene alkylphenyl ethers, and polyoxyethylene alkylphosphates; amphoteric surfactants, such as aminoacids, aminoalkylsulfonic acids, alkylbetaines, amineimides, and amine oxides; and cationic surfactants, such as alkylamine salts, aliphatic or aromatic quaternary ammonium salts, heterocyclic quaternary ammonium salts (e.g., pyridinium and imidazolium), and aliphatic or heterocyclic ring-containing phosphonium or sulfoniums.

Examples of such surfactants are described in U.S. Pat. Nos. 2,240,472, 2,831,766, 3,158,484, 3,210,191, 3,294,540, 3,507,660, British Pat. Nos. 1,012,495, 1,022,878, 1,179,290, 1,198,450, Japanese Patent Application (OPI) No. 117414/75, U.S. Pat. Nos. 2,739,891, 2,823,123, 3,068,101, 3,415,649, 3,666,478, 3,756,828, British Pat. No. 1,397,218, U.S. Pat. Nos. 3,133,816, 3,441,413, 3,475,174, 3,545,974, 3,726,683, 3,843,368, Belgian Pat. No. 731,126, British Pat. Nos. 1,138,514, 1,159,825, 1,374,780, Japanese Patent Publication Nos. 378/65, 379/65, 13822/68, U.S. Pat. Nos. 2,288,226, 2,944,900, 3,253,919, 3,671,247, 3,772,021, 3,589,906, 3,666,478, 3,754,924, West German Patent Application (OLS) No. 1,961,638, Japanese Patent Application (OPI) No. 59025/75, etc.

The following Examples are given to illustrate this invention in greater detail, although this invention is not limited thereto.

EXAMPLE 1

An aqueous silver nitrate solution and an aqueous potassium bromide solution were added at the same time to an aqueous gelatin solution maintained at 65° C. over a period of 50 minutes while maintaining pAg at 7.8 to prepare a silver bromide emulsion having an average grain size of $0.20\mu$. After the removal of soluble salts from the emulsion by the usual method, sodium thiosulfate and chloroauric acid were added to the emulsion, and the resulting mixture was subjected to chemical-aging at 65° C. for 60 minutes.

To the silver bromide emulsion were added 5-methylbenzotriazole, 4-hydroxy-6-methyl-1,3,3a,7-tetrazaindene, a dispersion of polyethyl acrylate, and a 2-hydroxy-4,6-dichloro-1,3,5-triazine sodium salt, and the thus-obtained mixture was divided into 12 portions.

Compounds II-2, II-16, Compounds I-1, I-3, I-16, and Comparative Compounds (a), (b) as shown below (comparative ones for Compound I) were added to the foregoing emulsion according to the formulations shown in Table 1 and coated on a polyethylene terephthalate film.

The thus-obtained film was brought into contact with a 150 line gray contact screen, exposed to light through a stage wedge for sensitometry, developed at 32° C. for 1 minute by the use of a developer having the composition shown below, stopped, fixed, washed with water, and dried.

COMPARATIVE COMPOUND (A)

6-tert-Butyl-2-(1-phenyl-5-mercaptotetrazolyl)hydroquinone

COMPARATIVE COMPOUND (B)

5-Nitroindazole

The dot quality was visually evaluated in grades (1) to (5). Grade (5) indicates the best dot quality and Grade (1), the worst. As a dot original for plate-making, only Grades (5) and (4) are usable.

The screen range is indicated by the difference between the logarithmic values of exposure amounts to provide blackened areas of 5% and 95%. As the difference is greater, the screen range is wide.

For comparison, the results obtained by combining a presently used lith light-sensitive element and lith development are shown: that is, Fuji Lith VO-100 available on the market was exposed in the same manner as described above and developed with Fuji Lith Developer HS-1 for a standard period of time (100 seconds at 27° C.). Since users are generally experienced with and accustomed to dot image formation using conventional lith system (i.e., conventional lith light-sensitive element and conventional lith developer), the system of this invention has preferably a screen range similar to that of the conventional lith system for easy handling of the system of this invention by users.

In order to confirm the stability of the developer, the developer was placed in a beaker and allowed to stand at room temperature for 3 days and, thereafter, it was used in the development processing. The results are also shown in Table 1.

TABLE 1

| Run No. | Compound II Type | Compound II Amount (mol/mol Ag) | Compound I Type | Compound I Amount* (mol/mol Ag) | Comparative Compound Type | Comparative Compound Amount (mol/mol Ag) | Just after Preparation of Developer Dot Quality | Just after Preparation of Developer Screen Range | After Allowing to Stand for 3 Days Dot Qualtiy | After Allowing to Stand for 3 Days Screen Range | Remarks |
|---|---|---|---|---|---|---|---|---|---|---|---|
| 1 | — | — | — | — | — | — | 1 | 1.45 | 1 | 1.45 | Comparison |
| 2 | — | — | I-1 | $6 \times 10^{-4}$ | — | — | 1 | 1.50 | 1 | 1.50 | " |
| 3 | II-2 | $4 \times 10^{-3}$ | — | — | — | — | 4 | 1.40 | 4 | 1.40 | " |
| 4 | " | " | I-1 | $6 \times 10^{-4}$ | — | — | 5 | 1.65 | 5 | 1.70 | Invention |
| 5 | " | " | I-3 | " | — | — | 5 | 1.60 | 5 | 1.65 | " |
| 6 | " | " | I-16 | " | — | — | 5 | 1.60 | 5 | 1.65 | " |
| 7 | " | " | — | — | a | $6 \times 10^{-4}$ | 4 | 1.35 | 4 | 1.30 | Comparison |
| 8 | " | " | — | — | b | " | 5 | 1.40 | 5 | 1.40 | " |
| 9 | II-16 | $1.5 \times 10^{-4}$ | — | — | — | — | 5 | 1.40 | 5 | 1.40 | " |
| 10 | " | " | I-1 | $6 \times 10^{-4}$ | — | — | 5 | 1.65 | 5 | 1.70 | Invention |
| 11 | " | " | I-16 | " | — | — | 5 | 1.60 | 5 | 1.65 | " |
| 12 | " | " | — | — | a | $6 \times 10^{-4}$ | 4 | 1.30 | 4 | 1.65 | Comparison |
| Reference: Fuji Lith VO-100 + Fuji Lith Developer HS-1 | | | | | | | 4 | 1.60 | 2 | 1.65 | Reference |

*The amount of Compound I added was determined so as to obtain the best dot quality.

| Composition of Developer 1 | |
|---|---|
| Hydroquinone | 15 g |
| Anhydrous Sodium Sulfite | 40 g |
| Potassium Bromide | 1 g |
| Polyethylene Glycol (average molecular weight: 1,500) | 3 g |
| 5-Nitroindazole | 50 mg |
| Boric Acid | 10 g |
| Sodium 2-Mercaptobenzimidazole-5-sulfonate | 300 mg |
| Water to make | 1 l |

The developer was adjusted to pH=11.5 with potassium hydroxide.

As apparent from Table 1, the use of compounds represented by formula (I) in combination with compounds represented by formula (II) provides high dot quality and wide screen range as compared with the case wherein only the compound represented by formula (II) is used (Run No. 3). Furthermore, it can be seen that in accordance with the method of this invention, high dot quality and wide screen range equal to or better than those obtained by the combination of the usual lith light-sensitive element and lith development (Reference Example) can be obtained and, moreover, a markedly stabilized developer can be used in comparison with the usual lith developer, and, therefore, constant dot quality and screen range can be obtained over a long period of time.

Furthermore, the dot quality and screen range obtained by using the compound represented by formula (I) in combination with the compound represented by formula (II) are improved over those obtained by using known hydroquinone derivative (a) and indazole compound (b) in combination with the compound represented by formula (II).

EXAMPLE 2

A silver bromide emulsion was prepared in the same manner as in Example 1. To the thus-obtained silver bromide emulsion were added 5-methylbenzotriazole, 4-hydroxy-6-methyl-1,3,3a,7-tetrazaindene, a dispersion of polyethyl acrylate, and a 2-hydroxy-4,6-dichloro-1,3,5-triazine sodium salt, and the resulting mixture was divided into 9 portions.

Compounds II-9, I-2, I-4, I-7, I-10, I-15, I-20, I-27 and I-30 were added to the foregoing emulsion according to the formulations shown in Table 2 and coated on a polyethylene terephthalate film.

The thus-obtained films were exposed and developed in the same manner as in Example 1, and their performance was evaluated by the same methods as used in Example 1.

The results are shown in Table 2.

having different halogen compositions as shown below:

| Emulsion A | AgBr |
| Emulsion B | AgBrI (I: 1 mol %) |
| Emulsion C | AgClBr (Br: 30 mol %) |
| Emulsion D | AgClBrI (Br: 30 mol %; I: 1 mol %) |

After the removal of soluble salts from the thus-obtained emulsions by the usual method, sodium thiosulfate was added to the emulsions, and the resulting mixtures were subjected to chemical aging at 60° C. for 70 minutes.

To each of the emulsions thus-obtained were added 4-hydroxy-6-methyl-1,3,3a,7-tetrazaindene, a dispersion of a styrene-butadiene copolymer, and a 2-hydroxy-4,6-dichloro-1,3,5-triazine sodium salt, and the resulting mixture was divided into 3 portions.

Compounds I-1 and II-21 were added according to the formulations shown in Table 3 and coated on a polyethylene terephthalate film.

The thus-obtained films were exposed and developed in the same manner as in Example 1, and their performance was evaluated by the same methods as used in Example 1.

TABLE 2

| Run No. | Compound II Type | Amount* (mol/mol Ag) | Compound I Type | Amount** (mol/mol Ag) | Dot Qualtiy | Screen Range | Remarks |
|---|---|---|---|---|---|---|---|
| 1 | II-9 | $3 \times 10^{-4}$ | — | — | 5 | 1.40 | Comparison |
| 2 | " | " | I-2 | $6 \times 10^{-4}$ | 5 | 1.60 | Invention |
| 3 | " | " | I-4 | $4 \times 10^{-4}$ | 5 | 1.60 | " |
| 4 | " | " | I-7 | $8 \times 10^{-4}$ | 5 | 1.55 | " |
| 5 | " | " | I-10 | $4 \times 10^{-4}$ | 5 | 1.60 | " |
| 6 | " | " | I-15 | $6 \times 10^{-4}$ | 5 | 1.60 | " |
| 7 | " | " | I-20 | $2 \times 10^{-3}$ | 4.5 | 1.50 | " |
| 8 | " | " | I-27 | $6 \times 10^{-4}$ | 5 | 1.60 | " |
| 9 | " | " | I-30 | $2 \times 10^{-4}$ | 5 | 1.70 | " |

*Amount to provide the highest dot quality.
**Amount to provide the widest screen range.

As apparent from Table 2, high dot quality and wide screen range can be obtained by the combination of this invention. Furthermore, it has been found that the excellent effects can be obtained by using any of the compounds represented by formula (I).

EXAMPLE 3

An aqueous silver nitrate solution and an aqueous halogen solution were added at the same time to an aqueous gelatin solution maintained at 57° C. over a period of 30 minutes to prepare silver halide emulsions The results are shown in Table 3.

TABLE 3

| Run No. | Composition of Emulsion | Compound II Type | Amount* (mol/mol Ag) | Compound I Type | Amount (mol/mol Ag) | Dot Qualtiy | Screen Range | Remarks |
|---|---|---|---|---|---|---|---|---|
| 1 | AgBr | — | — | — | — | 1 | 1.45 | Comparison |
| 2 | " | II-21 | $3 \times 10^{-3}$ | — | — | 5 | 1.40 | " |
| 3 | " | " | " | I-1 | $6 \times 10^{-4}$ | 5 | 1.65 | Invention |
| 4 | AgBrI | — | — | — | — | 2 | 1.40 | Comparison |
| 5 | " | II-21 | $2 \times 10^{-3}$ | — | — | 5 | 1.40 | " |
| 6 | " | " | " | I-1 | $6 \times 10^{-4}$ | 5 | 1.60 | Invention |
| 7 | AgClBr | — | — | — | — | 2 | 1.35 | Comparison |
| 8 | " | II-21 | $3 \times 10^{-3}$ | — | — | 5 | 1.35 | " |
| 9 | " | " | " | I-1 | $6 \times 10^{-4}$ | 5 | 1.60 | Invention |
| 10 | AgClBrI | — | — | — | — | 3 | 1.35 | Comparison |
| 11 | " | II-21 | $2 \times 10^{-3}$ | — | — | 5 | 1.35 | " |
| 12 | " | " | " | I-1 | $6 \times 10^{-4}$ | 5 | 1.60 | Invention |

*The amount of Compound II added was determined so that the highest dot quality was obtained.

As can be seen from Table 3, the screen range widening effect by the combination of this invention can be obtained for an emulsion having any halogen composition.

While the invention has been described in detail and with reference to specific embodiments thereof, it will be apparent to one skilled in the art that various changes and modifications can be made therein without departing from the spirit and scope thereof.

What is claimed is:

1. A method for forming a photographic image which comprises imagewise exposing a silver halide photographic light-sensitive element having a silver halide emulsion layer of substantially the surface latent image type, said silver halide emulsion layer or at least one member of other hydrophilic colloid layers containing a compound represented by formula (I) below, and developing the exposed light-sensitive element in the presence of a compound represented by formula (II) below:

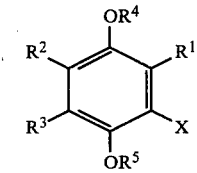

wherein

X is an indazole radical which is linked to the benzene nucleus through the nitrogen atom at the 1- or 2-position thereof and which may be substituted;

$R^1$, $R^2$ and $R^3$ may be the same or different and each represents a hydrogen atom, an alkyl group, an aryl group, an alkylthio group, an arylthio group, a halogen atom, a hydroxy group, an alkoxy group, an aryloxy group, an acyl group, an alkoxycarbonyl group, an amido group, a sulfonamido group, a carbamoyl group, a sulfamoyl group, a heterocyclic radical, or X, and $R^2$ and $R^3$ may combine together to form a ring;

$R^4$ and $R^5$ each represents a hydrogen atom or a group which is hydrolyzed in the presence of an alkali;

wherein $R^6$ represents an aryl group which may be substituted, and $R^7$ represents a hydrogen atom, an aryl group which may be substituted, or an alkyl group which may be substituted.

2. The method for forming a photographic image as claimed in claim 1, wherein a substituent for the indazole radical is a nitro group, an amino group, a carboxy group, a cyano group, a halogen atom, a hydroxy group, an alkyl group, an alkoxy group, an alkoxycarbonyl group, an alkylthio group, an acyl group, a sulfamoyl group, a carbamoyl group, an amido group or an acyloxy group.

3. The method for forming a photographic image as claimed in claim 1, wherein a substituent for the indazole radical is a nitro group, a cyano group or a halogen atom.

4. The method for forming a photographic image as claimed in claim 1, wherein X is a 5-nitroindazole group.

5. The method for forming a photographic image as claimed in claim 1, wherein $R^1$, $R^2$ and $R^3$ are each hydrogen, an alkyl group, an aryl group, an alkylthio group, a halogen atom, an alkoxy group, a carbamoyl group or X.

6. The method for forming a photographic image as claimed in claim 1, wherein a ring which is formed by bonding $R^2$ and $R^3$ each other is a naphthohydroquinone ring, a 5,6-tetramethylenehydroquinone ring or a 5,6-(1,3-cyclopentylenyl)hydroquinone ring.

7. The method for forming a photographic image as claimed in claim 1, wherein said group capable of being hydrolyzed in the presence of an alkali is an acyl group, a halogen-substituted acyl group, an alkoxycarbonyl group or an aryloxycarbonyl group.

8. The method for forming a photographic image as claimed in claim 1, wherein $R^4$ and $R^5$ are each hydrogen.

9. The method for forming a photographic image as claimed in claim 1, wherein said compound represented by formula (I) is Compound I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33 or I-34.

10. The method for forming a photographic image as claimed in claim 1, wherein said compound represented by the formula (I) is Compound I-1, I-2, I-3, I-4, I-7, I-10, I-12, I-15, I-16, I-20, I-27 or I-30.

11. The method for forming a photographic image as claimed in claim 1, wherein said compound represented by formula (I) is incorporated in said silver halide emulsion layer.

12. The method for forming a photographic image as claimed in claim 1, wherein said compound represented by formula (I) is incorporated in said hydrophilic colloid layer.

13. The method for forming a photographic image as claimed in claim 12, wherein said hydrophilic colloid layer is an undercoat layer, an overcoat layer, a protective layer or an intermediate layer.

14. The method for forming a photographic image as claimed in claim 1, wherein the amount of said compound represented by formula (I) is from about $10^{-6}$ to $10^{-1}$ mol/mol Ag.

15. The method for forming a photographic image as claimed in claim 1, wherein $R^6$ is a benzene ring or a naphthalene ring.

16. The method for forming a photographic image as claimed in claim 1, wherein $R^6$ is a benzene ring.

17. The method for forming a photographic image as claimed in claim 1, wherein $R^7$ is a hydrogen atom, a methyl group, an ethyl group, an n-propyl group, an isopropyl group, a phenyl group, a 4-chlorophenyl group, a 4-bromophenyl group, a 3-chlorophenyl group, a 4-cyanophenyl group, a 4-carboxyphenyl group, a 4-sulfophenyl group, a 3,5-dichlorophenyl group or a 2,5-dichlorophenyl group.

18. The method for forming a photographic image as claimed in claim 1, wherein $R^7$ is a hydrogen atom, a methyl group or a phenyl group.

19. The method for forming a photographic image as claimed in claim 1, wherein $R^7$ is a hydrogen atom.

20. The method for forming a photographic image as claimed in claim 1, wherein said compound represented by formula (II) is incorporated in said silver halide photographic light-sensitive element in an amount of from about $10^{-8}$ to $10^{-1}$ mol/mol Ag.

21. The method for forming a photographic image as claimed in claim 1, wherein said compound represented by formula (II) is incorporated in a prebath prior to development processing or a development processing solution in an amount of from about 5 mg to 5 g per liter of the prebath or developing processing solution.

* * * * *